United States Patent [19]

Qureshi et al.

[11] Patent Number: 4,859,422
[45] Date of Patent: Aug. 22, 1989

[54] ANALYSIS SYSTEM

[75] Inventors: Humayun Qureshi, Wayland; Stanley M. Liffmann, Andover; Milo E. Webster, Braintree; Theodore S. Geiselman, Groveland, all of Mass.

[73] Assignee: Fisher Scientific Company, Pittsburgh, Pa.

[21] Appl. No.: 75,052

[22] Filed: Jul. 17, 1987

[51] Int. Cl.⁴ .............................................. G01N 35/00
[52] U.S. Cl. ........................................ 422/81; 436/52
[58] Field of Search .................................... 422/63–68, 422/81, 100; 137/884, 597, 559; 251/331; 436/52

[56] References Cited

U.S. PATENT DOCUMENTS

| | | | |
|---|---|---|---|
| 4,013,413 | 3/1977 | Stewart et al. | 422/81 |
| 4,177,677 | 12/1979 | Ruzicka et al. | 422/82 |
| 4,304,257 | 12/1981 | Webster | 251/331 |
| 4,315,754 | 2/1982 | Ruzicka et al. | 422/81 |
| 4,504,443 | 3/1985 | Hansen et al. | 422/81 |
| 4,546,088 | 10/1985 | Karlberg et al. | 422/82 |
| 4,601,881 | 7/1986 | Webster | 422/67 |
| 4,607,526 | 8/1986 | Bachenheimer et al. | 422/81 |
| 4,640,821 | 2/1987 | Mody et al. | 422/82 |

OTHER PUBLICATIONS

Ruzicka, Jaromir, *Analytical Chemistry*, "Flow Injection Analysis from Test Tube to Integrated Microconduits", vol. 55, No. 11 (Sep. 1983).

Primary Examiner—Michael S. Marcus

[57] ABSTRACT

An analysis system includes sample insertion module structure with structure defining a reduced pressure reservoir, structure defining a sample region, and structure defining a reagent circuit that includes metering chamber structure in series with the reagent circuit. First transfer valve structure is arranged to couple the sample region to the reagent circuit on one side of the metering chamber structure, and second transfer valve structure is arranged to couple the reagent circuit to the reduced pressure reservoir structure on the side of the metering chamber structure remote from the first transfer valve structure for inserting an intact metered quantity of sample liquid into a reagent stream.

18 Claims, 3 Drawing Sheets

ANALYSIS SYSTEM

This invention relates to liquid handling systems and to apparatus for the analysis of fluid samples, and has particular application to apparatus for the analysis of constituents of biological fluids such as blood.

Chemical analyses are conducted in a variety of fields, and the need for such analyses has given rise to development of a variety of analysis systems. Among such analyzer systems are systems in which a sample of the liquid is inserted into a nonsegmented carrier stream of a reagent. The inserted sample and the reagent interact as the reagent stream is flowed to a utilization device such as a detector. A variety of slide and rotary valve arrangements and flow systems have been proposed for analyzer systems of this type, which is sometimes termed flow injection analysis.

In accordance with one aspect of the invention, there is provided a liquid handling system useful in apparatus for analyzing biological liquid specimens or the like which includes structure defining a reduced pressure reservoir, structure defining a sample region and structure defining a reagent circuit that includes metering chamber structure in series with the reagent circuit. First transfer valve structure couples the sample region to the reagent circuit on one side of the metering chamber structure and second transfer valve structure couples the reagent circuit to the reduced pressure reservoir structure on the other side of the metering chamber. Reduced pressure from the reservoir structure is applied through the second transfer valve structure to reduce pressure in the metering chamber structure for drawing sample from the sample region through the first transfer valve into the metering chamber structure for inserting a quantity of the sample to be analyzed as a plug into a stream of reagent liquid in the reagent circuit. The reagent stream with the inserted sample liquid is flowed as an intact bubble-free composite stream to a utilization device which may be a sensor (for example, colorimetric, ion selective, or polarographic) module, or an intermediate device such as a gas diffusion unit. The system provides rapid insertion of sample liquid into a reagent liquid stream without introduction of bubbles ahead of or behind the sample slug, in a simple and mechanically reliable arrangment.

In preferred embodiments, the reagent circuit is connected to a source of reagent liquid that is flowed through the reagent circuit, and in a particular embodiment, the utilization device includes a gas diffusion unit that is connected to the reagent circuit, the gas diffusion unit having a reagent liquid portion and a buffer liquid portion that are separated from each other by a membrane. A gaseous constituent produced by the reaction of the reagent liquid with the sample material diffuses across the membrane into the buffer liquid stream for transport to an analysis unit, the reagent liquid and buffer liquid streams being concurrently flowed through the gas diffusion unit at correlated flow rates by positive displacement pumps. Examples of reactions that yield a volatile gas include the reaction of serum with an acid to release sodium bicarbonate, sodium carbonate, and protein bound carbon dioxide; the reaction of urea with urease to release ammonia and carbon dioxide; and the reaction of creatinine with creatinine iminohydrolase to release ammonia; the reaction of oxalosuccinate with isocitrate dehydrogamase to release ammonium; and the reaction of L'glutamate and AND+with glutamate dehydroganase and water to release ammonia.

In a particular embodiment, the sample region, the reagent circuit including the metering chamber, and the reduced pressure reservoir structures, are in a sample insertion module that includes a face plate member with a firm and stable surface, and a flexible sheet member that has a softer and more resilient surface is clamped into con engagement to the firm and stable face plate surface. A flow channel network is formed in one of the engaged surfaces together with valve land portions that separate adjacent flow channel portions. Each valve also includes an actuator which is arranged to flex the sheet member between a first position in which the surface of the valve sheet member is in mating and sealing engagement with the surface of the face plate member so that the valve land portion blocks flow between the adjacent channel portions, and a second position in which the sheet surface is spaced from the first position and allows liquid flow across the land portion between adjacent channel portions of the sample region and the reagent circuit. Each valve has a small volume when open and essentially zero dead space when closed. Each transfer valve includes the parallel channels spaced by a land that extends across the valve site. The gentle and smooth closing action of the valve membrane is in a radially inward direction and the transfer valves provide rapid transfer of liquid from the sample circuit to the reagent circuit and reproducible contacting between different liquids in the sample region and reagent circuit.

Other features and advantages of the invention will be seen as the following description of a particular embodiment progresses, in conjunction with the drawings in which.

DESCRIPTION OF PARTICULAR EMBODIMENT

Figure 1:
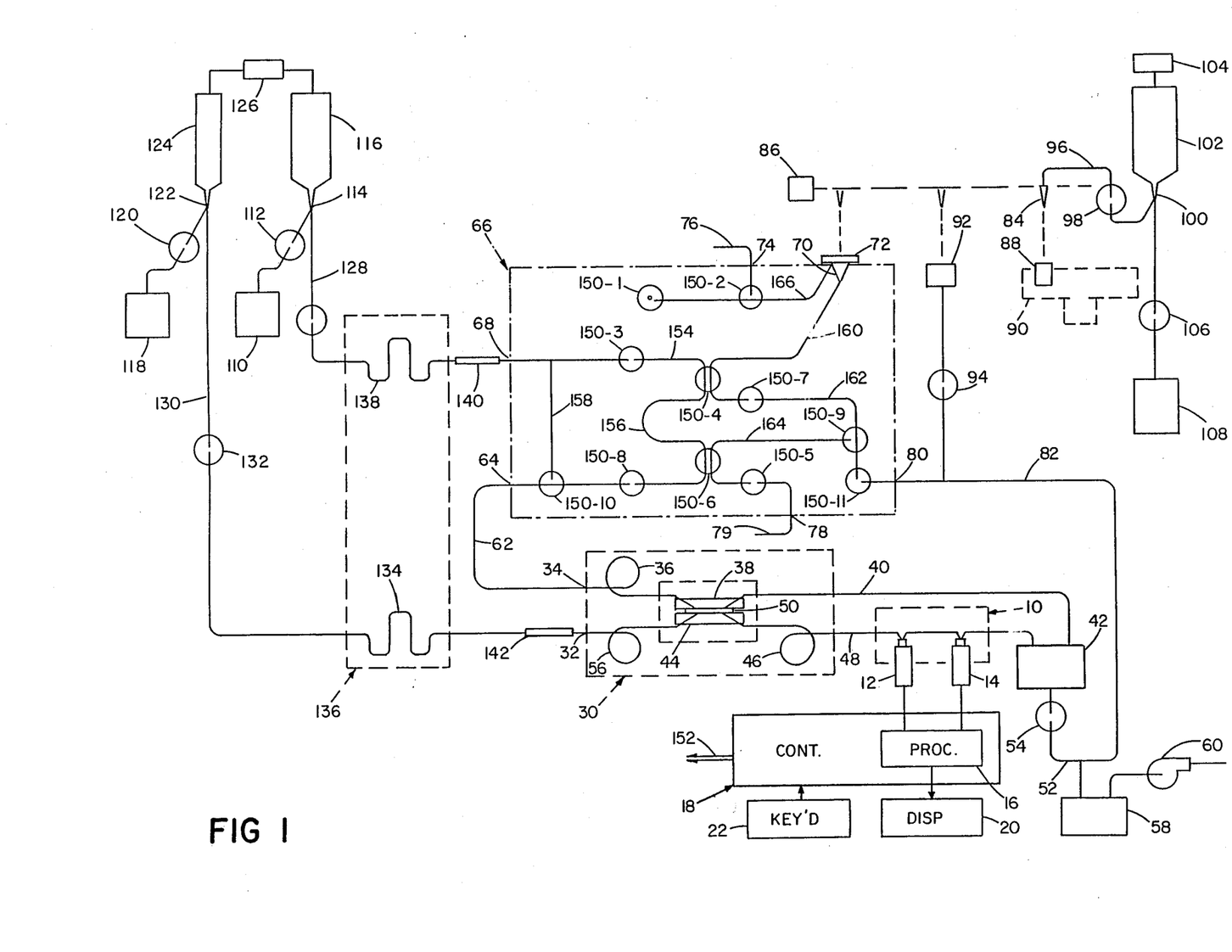
FIG. 1 is a diagrammatic view of an analysis system in accordance with the invention for measuring total carbon dioxide in a biological liquid such as serum or plasma.

Shown in FIG. 1 is a diagrammatic view of an analyzer system for measuring total carbon dioxide in samples of biological liquids such as serum or plasma that includes analysis unit 10 that has pH electrode 12 and reference electrode 14 that are connected to processor 16 in system controller 18. Processor 16 is connected to apply outputs to display 20 and controller 18 has inputs from keyboard 22. That analyzer system is incorporated in a system for measuring other parameters biological fluids, and further aspects of that system may be seen reference to copending application Ser. No. 074,882 entitled SAMPLE ANALYSIS , and Ser. No. 074,942 entitled LIQUID HANDLING, and filed concurrently herewith, the disclosures of which are specifically incorporated herein by reference.

Coupled to analysis unit 10 is gas diffusion unit 30 that has inlet 32 for buffer liquid stream and inlet 34 for an reagent liquid stream into which a sample to be analyzed has been inserted. The reagent liquid flows from inlet 34 through tubing coil 36, diffusion channel structure 38 and line 40 to drip isolator 42. The buffer liquid similarly flows from inlet 32 through tubing coil 43 and diffusion channel structure 44. Clamped between diffusion channel structures 38 and 44 is diffusion membrane 50 across which gas diffuses from the reagent stream to the buffer stream. The buffer stream then flows through optional coil 46 and line 48 to analysis unit 10 for sensing by pH and reference electrodes 12 and 14 and then is discharged to drip isolator 42 to which atmospheric pressure is at nine inches of mercury from manifold 52 is applied under control of valve 54 to empty drip isolator 42. Chamber 58 and pump 60 apply reduced pressure to manifold 52.

Coupled to inlet port 34 of gas diffusion unit 30 via line 62 is outlet port 64 of sample insertion module 66. Module 66 has a reagent liquid inlet port 68, a sample chamber 70 that is closed by valve 72, input 74 from a source of buffer liquid over line 76, input 78 from a source of reagent over line 79, and outlet 80 that is connected by line 82 to the reduced pressure manifold 52.

A sample introduction system includes sample probe 84 that is mounted for movement by drive 86 between a sample container 88 (an array of sample containers 88 being disposed on turntable 90), wash cup 92 (that is connected to vacuum manifold 52 via valve 94), and valve 72 of sample chamber 70 of sample insertion module 66. Further details of valve 72 and the probe system may be seen with reference to copending applications Ser. No. 074,921, entitled FLUID HANDLNG and Ser. No. 074,942, entitled LIQUID HANDLING, filed concurrently herewith, the disclosures of which are specifically incorporated herein by reference. Sample probe 84 is connected via line 96 and valve 98 to the outlet 100 of metering syringe pump 102 whose piston is operated by stepper motor 104. Pump outlet 100 is also connected via valve 106 to reservoir 108 of de ionized water.

A source 110 of reagent liquid (nine millimol per liter sulfuric acid) is connected via valve 112 to outlet 114 of one milliliter capacity syringe pump 116; and a source 118 of buffer liquid (twelve millimol per liter sodium bicarbonate) is connected via valve 120 to outlet 122 of one half milliliter capacity syringe pump 124. Common stepper motor drive 126 moves the pistons of syringe pumps 116 and 124 in synchronism to provide concurrent flow of acid reagent and buffer liquid from the outlets of pumps 116 and 124 over lines 128, 130, respectively, the reagent liquid flow rate being twice that of the buffer liquid. Line 130 is connected via valve 132 to preheater coil 134 in preheater unit 136 that is maintained at a temperature of about 36° C. and line 128 is connected via valve 137 to a similar preheater coil 138 in preheater unit 136. The heated reagent and buffer liquids are concurrently flowed from preheater unit 136 through Goretex vent tube sections 140, 142 to inlet 68 of the sample insertion module 66 and inlet 32 of the gas diffusion unit 30, respectively.

Sample insertion module 66 includes an array of valves 150 of the type shown in Webster U.S. Pat. 4,304,257 and Webster U.S. Pat. No. 4,601,881, the disclosures of which are also specifically incorporated herein by reference, valves 150 (and valves 54, 94, 98, 106, 112, 120, 132 and 137) being operated by signals over lines 152 from controller 18. Sample insertion module 66 includes a reagent circuit 154 that extends from isolation valve 150 3, through transfer valve 150-4, metering chamber passage 156 (of ten microliter volume), transfer valve 150-6, isolation valve 150 8 and shunt valve 150 10 to outlet 62. Shunt circuit 158 is controlled by valve 150-10, reagent circuit 154 and metering chamber 156 being shunted when valve 150-10 is operated to open the shunt path from inlet 68 to outlet 64. A sample circuit 160 extends from sample chamber 70 through transfer valve 150-4 and isolation valve 150-7 to reduced pressure reservoir channel 162 that is coupled by isolation valve 150-11 to outlet 80 that is connected to vacuum manifold 52 over line 82. Channel region 162 between isolation valves 150-7 and 150-11 provides a reduced pressure reservoir for controlled flow of liquid. Auxiliary circuit 164 extends from isolation valve 150-5 through transfer valve 150-6 to selector valve 150-9 that connects the auxiliary circuit 164 to the reduced pressure reservoir circuit 162. (Sample channel 160 extends below auxiliary channel 164 as indicated at 160A in FIG. 3.) A vent circuit 166 extends from the top of sample chamber 70 through selector valve 150-2 to vent valve 150-1. When valve 150-2 is open, buffer solution may be applied to vent circuit 166, sample chamber 70 and sample circuit 160; and when isolation valve 150-5 is opened, reagent may similarly be applied to auxiliary circuit 164.

Figure 2:
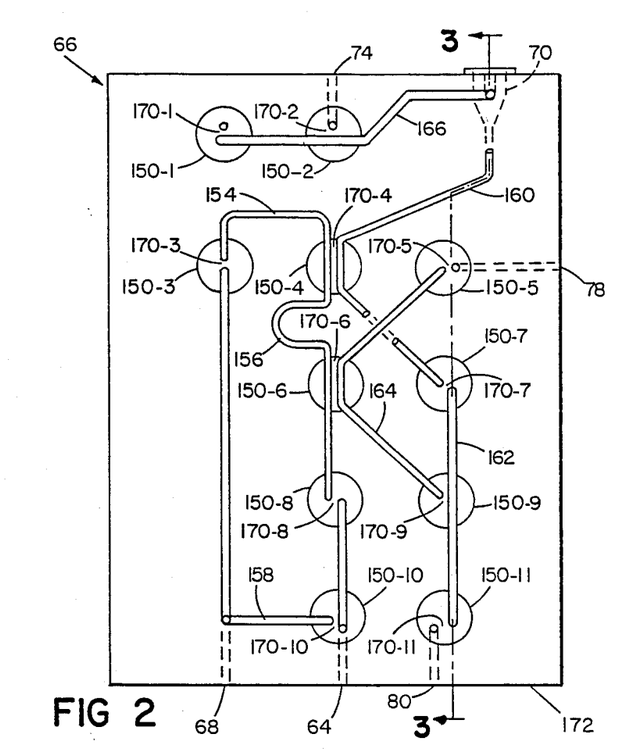
FIG. 2 is a diagrammatic front view of sample insertion apparatus employed in the system shown in FIG. 1.
Figure 3:
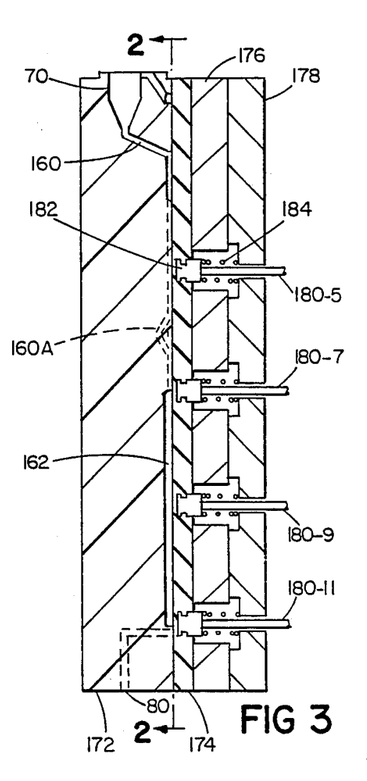
FIG. 3 is a sectional view taken along the line 3—3 of FIG. 2.

Further details of sample insertion module 66 may be seen with reference to Figs. 2 and 3. That module includes acrylic face plate 172. Sheet membrane 174 is clamped against the rear surface of face plate 172 by backer plate 176 and structure 178 supports an array of electric solenoids (not shown) that operate actuators 180. Each actuator has a head 182 that is embedded in the membrane sheet 174 at a valve position and a spring 184 seated between the actuator head 182 and support plate 178 maintains the membrane 174 in seated valve closed position against the lands 170 of the respective transfer, selector, isolation and vent valves. Energization of its electric solenoid moves the actuator 180 away from face plate 172 and opens the valve to permit flow of fluid across the valve land 170. Upon the de energization of the solenoid, the spring 184 moves the actuator 180 towards the face plate 172 in a gentle and smooth closing action with the membrane 174 moving in a radially inward direction so that there is essentially zero dead space when the valve is closed and excellent isolation between liquids in adjacent channels is provided. Metering chamber 156 of about ten microliters volume is formed by the reagent circuit channel section between the transfer valves 150-4 and 150-6.

The reagent circuit 154 is provided by a channel in the acrylic face plate 172 that has a width of 0.8 millimeter and a depth of about one half millimeter. Sample circuit 160 and auxiliary circuit 164 each includes a parallel channel through the corresponding transfer valve that has a depth of about half millimeter and a width of about one half millimeter. Channels 154 and 160 are spaced apart by land 170-4 of valve 150-4 that has a width of less than one millimeter, and the lands 170 of the other valves are of similar width.

Figure 4:
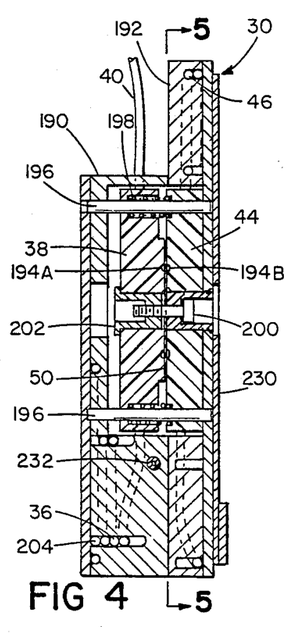
FIG. 4 is a sectional view taken along the line 4—4 of FIG. 5 showing aspects of gas diffusion apparatus employed in the system shown in FIG. 1.
Figure 5:
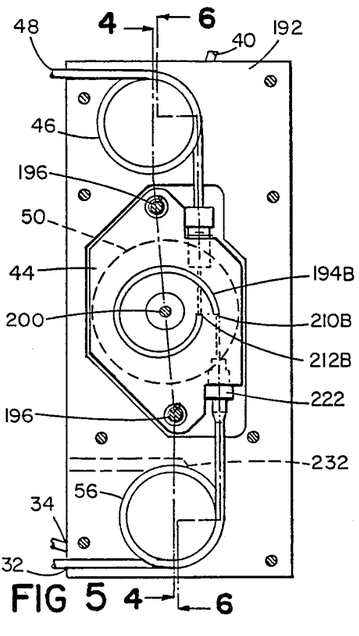
FIG. 5 is a sectional view taken along the line 5—5 of FIG. 4.
Figure 6:
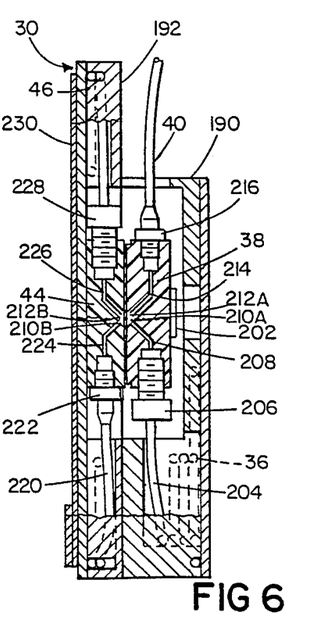
FIG. 6 is a sectional view taken along the line 6—6 of FIG. 4.

Further details of the gas diffusion assembly 30 may be seen reference to FIGS 4–6. That diffusion assembly includes aluminum housing members 190, 192 which receive acrylic diffusion channel structures 38, 44, each of which has a spiral flow channel 194 formed on its surface, each channel 194 having a length of about eight centimeters, a width of about two millimeters and a depth of about 0.2 millimeter. Guide posts 196 extend between housing members 190, 192 and position diffusion channel structures 38, 44 with the flow channels 194A, 194B in alignment. Springs 198 on guide posts bias the diffusion channel structures apart, and cooperating threaded fastener members 200, 202 clamp the adjacent juxtaposed surfaces of diffusion channel structure 38, 42 against membrane 50 that is a disc of 0.2 micron expanded polytetrafluorethylene and has a diameter of about four centimeters. Housing member 190 has a chamber region in which 0.5 millimeter ID Teflon reagent tubing 204 extends from inlet 34 through a three turn coil 36 of about 2½ centimeter diameter, tube fitting 206 which is coupled to 0.5 millimeter diameter flow channel 208 that extends to inlet end 210A of the spiral channel 194A. The outlet end 212A of channel 194A is connected through channel 214 and fitting 216 to tube 40. The buffer fluid tube 220 is coupled by fitting 222 and channel 224 to inlet end 210B of flow channel 194B and its outlet end 212B is coupled by channel 226 and fitting 228 through optional tubing coil 46 and line 48 to measurement module 10 for flow of the transport buffer past pH electrode 12 and reference electrode 14. Heater pad 230 is mounted on housing member 192 and thermistor 232 is embedded in housing block 190 to monitor the temperature of the diffusion gas assembly 30, controller 18 maintaining the temperature of assembly 30 at 35° C.

Figure 7A:
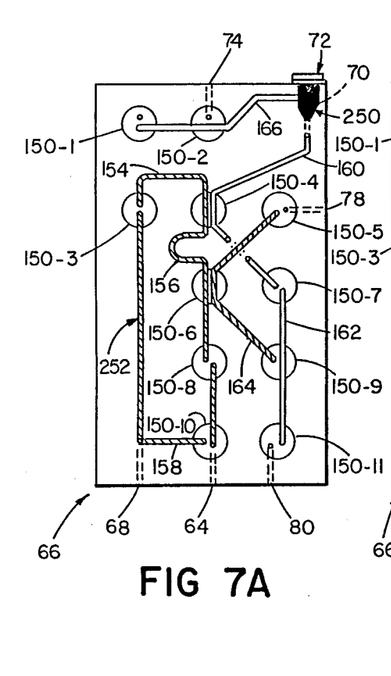
FIGS. 7A–7B are a series of diagrammatic views showing an operational sample insertion sequence employed in the system shown in FIG. 1.
Figure 7B:
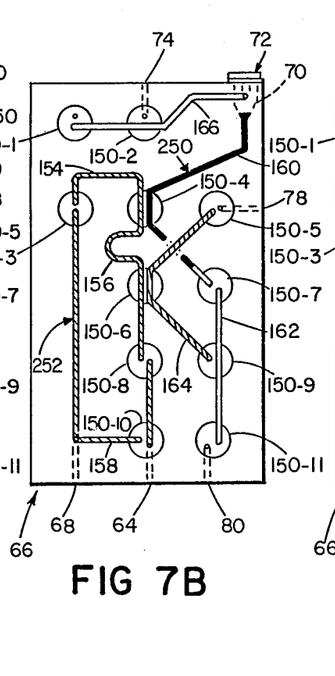

Details of a sample insertion sequence may be seen with reference to FIG. 1 and the series of module diagrams of FIGS. 7A–7D. At the start of an analysis cycle, probe 84 (FIG. 1) (that has previously been filled with diluent from reservoir 108) is rinsed at wash cup 92 and then is moved to the sample station to draw up about two microliters of air and then an appropriate quantity (depending on analyses to be preformed at other modules of the system) of sample from sample cup 88. Probe 84 is then moved by drive 86 to the sample insertion module 66 where valve 72 is opened and a thirty five microliter volume of sample 250 is injected into chamber 70 (as indicated in FIG. 7A) by pump 102. During this interval, buffer syringe pump 124 has been filled with one half milliliter of bicarbonate buffer and reagent syringe pump 116 has been filled with one milliliter of sulfuric acid reagent (see FIG. 1). In a preflush sequence 300 microliters of acid and 150 microliters of buffer are flowed by operation of the syringe drive 126 through preheater 136 to shunt circuit 158 through valve 150-10 to gas diffusion assembly 30. Since valves 150-3 and 150-8 are closed during this preflush, reagent 252 is immobilized in the reagent circuit 154 and metering chamber 156. Vent valve 150-1 is opened to expose the surface of sample 250 in chamber 70 to atmosphere. After manifold channel 162 has been charged with nine mm Hg reduced pressure, valve 150-11 is closed to trap that reduced pressure in manifold channel 162 and valve 150-7 is opened so that the reduced pressure draws sample 250 from chamber 70 along sample channel 160 through transfer valve 150 4 (which is not open at this time) toward isolation valve 150-7. Valve 150-7 is then closed, the reservoir channel 162 is recharged with reduced pressure and the cycle repeated to draw sample 250 further toward valve 150-7 as indicated in FIG. 7B.

Figure 7C:
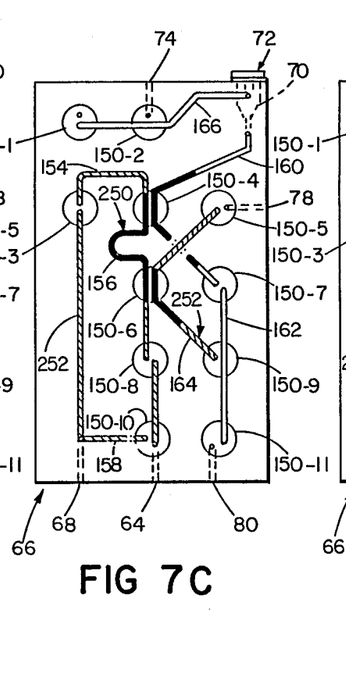

After completion of flowing of sample 250 through sample channel 160, past valve site 150-4 towards valve 150-7, reservoir channel 162 is again recharged. Transfer valves 150-4 and 150-6 and control valve 150 9 are then opened, and the reduced pressure in channel 162 draws reagent 252 from metering chamber 156 into auxiliary channel 164 and replaces that reagent with sample 250 from the sample channel 160. Transfer valves 150 , 150-6 are then closed. As indicated in FIG. 7C, isolating leading and trailing edge portions of the sample 250 in channels 160 and 164 with a guantity of sample 250 inserted into the metering chamber portion 156 of the reagent circuit 154 as a plug (and without air bubble isolation or segmentation) into the reagent stream 252.

Figure 7D:
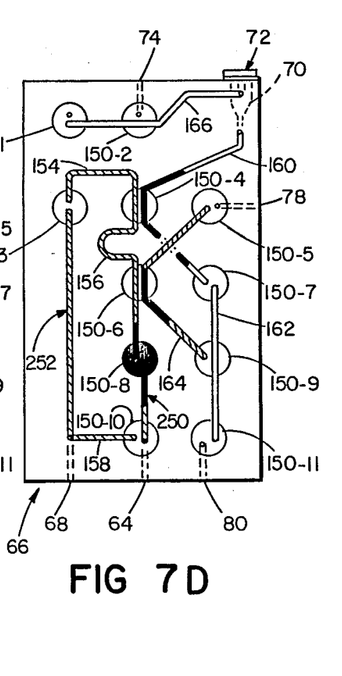

After this transfer, syringe pumps 116 and 124 are operated synchronously by drive 126 for about twenty four seconds to flow reagent 252 at a 1.1 milliliter per minute reagent flow rate through inlet 68 and outlet 64 via shunt circuit 158, and a corresponding flow of buffer at a 0.56 milliliter per minute rate to gas diffusion unit 30. One hundred milliseconds after pumps 116 and 124 start, valves 150-3 and 150-8 are opened and fifty microseconds later, valve 150-10 is closed to interrupt the shunt channel 158 so that the reagent circuit with the inserted sample 250 is flowed (as indicated in FIG. 7D) along tube 62 and through mixing coil 36 diffusion channel structure 38. During that transport interval, the acid reagent 252 and sample 250 are subjected to radial dispersion and bolus mixing and the acid in reagent 252 reacts with serum in sample 250 in the flowing stream to produce carbonic acid which releases carbon dioxide. The released carbon dioxide in the reagent stream in flow channel 194A (FIGS. 4–6) diffuses across membrane 50 into the sodium bicarbonate buffer stream in flow channel 194B for transport past the pH and reference electrodes 12 and 14 at a positive buffer flow rate of 0.56 milliliter per minute.

Controller 18 begins a data acquisition sequence about three seconds before the peak output signal to establish a base line and data acquisition continues for about ten seconds such that the output signal is followed past its maximum. The peak height is found by averaging five data points at a time and then taking the highest and lowest average of those data points. The difference between the base line (lowest average) and peak (highest average) is the delta or peak height which is directly proportional to total carbon dioxide concentration in the sample being analyzed.

After completion of the data acquisition interval, the syringe pumps 116, 124 flow acid and buffer at a 4.7 milliliter per minute acid flow rate (2.35 millimeter buffer flow rate) for about eight seconds to flush the system, reagent being also flowed through port 78 and isolation valve 150-5 under the influence of reduced pressure from manifold 52 to flush the auxiliary channel 164. Buffer solution is similarly drawn by reduced pressure through port 74 and selector valves 150-2, 150-7 and 150-11 to flush sample line 160 and sample chamber 70. Vent valve 150-1 is then opened and selector valve 150-2 closed to dry the sample chamber 70 and sample line 160, and the system is ready for the next cycle.

While a particular embodiment of the invention has been shown and described, various modifications will be apparent to those skilled in the art, and therefore it is not intended that the invention be limited to the disclosed embodiment or to details thereof, and departures may be made therefrom within the spirit and scope of the invention.

What is claimed is:

1. Apparatus for analyzing specimens of biological fluids and the like comprising,
   structure defining a reduced pressure reservoir,
   structure defining a sample region,
   structure defining a reagent circuit that includes metering chamber structure in series in said regent circuit,
   first transfer valve structure in said reagent circuit on one side of said metering chamber structure for coupling said sample region to said reagent circuit through a first path separate from said reagent circuit, said first transfer valve structure defining one boundary of said metering chamber structure,
   second transfer valve structure in said reagent circuit on the side of said metering chamber structure opposite said one side for coupling said reagent circuit to said reduced pressure reservoir structure through a second path separate from said reagent circuit, said second transfer valve structure defining a second boundary of said metering chamber structure.
   means for applying reduced pressure from said reservoir structure through said second transfer valve structure to reduce the pressure in said metering chamber structure for drawing reagent from said metering chamber structure out of said reagent circuit through said second transfer valve structure and said second path and concurrently drawing sample from said sample region through said first transfer valve structure into said metering chamber structure for replacing the guantity of regent drawn out of said metering chamber structure with a guantity of sample to be analyzed as a plug in a stream of reagent liquid in said reagent circuit; and
   flow control means including means connecting said reagent circuit to a utilization device and means for flowing a reagent stream including an inserted plug of sample material from said reagent circuit to said utilization device.

2. The apparatus of claim 1 wherein said apparatus includes a sample insertion module with a face plate member that has a rigid surface,
   a flexible valve sheet member that has a surface that is softer and more resilient than said said face plate member for mating engagement with said face plate surface,
   a network of channel portions in one of said members with a plurality of valve land portions, each said valve land portion being located between adjacent ones of said channel portions, the surfaces of said land portions being coincident with the surface of the member in which they are located,
   one of said channel portions defining said reduced pressure reservoir structure, a second one of said channel portions defining said reagent circuit, and a third of said channel portions defining a sample channel, a portion of said reagent circuit channel and a portion of said sample channel extending through a valve region with a valve land between said adjacent channel portions and defining said first transfer valve structure.

3. The apparatus of claim 2 wherein each said transfer valve structure includes two parallel channels that extend through a valve region with a valve land extending through said valve region between said two parallel channels.

4. Apparatus for analyzing specimens of biological fluids and the like comprising,
   structure defining a reduced pressure reservoir,
   structure defining a sample region,
   structure defining a reagent circuit that includes metering chamber structure in series in said reagent circuit,
   first transfer valve structure in said reagent circuit on one side of said metering chamber structure for coupling said sample region to said reagent circuit,
   second transfer valve structure in said reagent circuit on the side of said metering chamber structure opposite said one side for coupling said reagent circuit to said reduced pressure reservoir structure,
   means for applying reduced pressure from said reservoir structure through said second transfer valve structure to reduce the pressure in said metering chamber structure for drawing reagent from said metering chamber structure through said second transfer valve structure and concurrently drawing sample from said sample region through said first transfer valve structure into said metering chamber structure for replacing a guantity of reagent with a guantity of sample to be analyzed as a plug in a stream of reagent liquid in said reagent circuit;
   a gas diffusion unit connected to said reagent circuit, said gas diffusion unit including structure defining a reagent flow path, structure defining a buffer liquid flow path, and membrane structure interposed between said reagent flow and said buffer liquid flow paths,
   means for concurrently flowing a buffer liquid stream through said buffer liquid flow path and said reagent liquid stream with said inserted sample guantity through said reagent flow path so that a gaseous constituent released by interaction of said sample material and said reagent material diffuses across said membrane into said buffer liquid stream, and
   means for analysis of said diffused gaseous constituent as a function of a constituent of interest of said sample.

5. The apparatus of claim 4 wherein said means for concurrently flowing a buffer liquid stream through said buffer flow path and said reagent liquid stream with said inserted sample quantity through said reagent flow path includes positive displacement pump means.

6. The apparatus of claim 5 wherein said positive displacement pump means includes first pump means for said buffer liquid stream and second pump means for said reagent liquid stream, and common drive means for said first and second pump means.

7. The apparatus of claim 5 wherein said first and second positive displacement pump means is each of the piston type.

8. The apparatus of claim 4 wherein said analysis means includes a pH electrode and a reference electrode.

9. Sample insertion module structure comprising structure defining a reduced pressure reservoir, structure defining a sample region, structure defining a reagent circuit that includes metering chamber structure in series with said reagent circuit, first transfer valve structure in said reagent circuit on one side of said metering chamber structure for coupling said sample region to said reagent circuit through a first path separate from said reagent circuit, said first transfer valve structure defining a first boundary of said metering chamber structure, and second transfer valve structure in said reagent circuit on the side of said metering chamber structure remote from said first transfer valve structure for coupling said reagent circuit to said reduced pressure reservoir structure through a second path separate from said reagent circuit, said second transfer valve structure defining a second boundary of said metering chamber structure.

10. The module structure of claim 9 wherein said module structure includes a face plate member that has a rigid surface,
- a flexible valve sheet member that has a surface that is softer and more resilient than said face plate member for mating engagement with said face plate surface,
- a network of channel portions in one of said members with a plurality of valve land portions, each said valve land portion being located between adjacent ones of said channel portions, the surfaces of said land portions being coincident with the surface of the member in which they are located,
- one of said channel portions defining said reduced pressure reservoir structure, a second one of said channel portions defining said reagent circuit, and a third of said channel portions defining said sample 18 region, a portion of said reagent circuit channel and a portion of said sample channel extending through a valve region with a valve land between said adjacent channel portions and defining said first transfer valve structure.

11. The module structure of claim 9 wherein each said transfer valve structure includes two parallel channels that extend through a valve region with a valve land extending through said valve region between said two parallel channels.

12. An analysis system comprising
analysis structure that has an inlet,
- gas diffusion unit including structure defining a reagent flow path, structure defining a buffer liquid flow path, and membrane structure interposed between said reagent flow and buffer liquid flow paths,
- sample insertion module structure including structure defining a reduced pressure reservoir, structure defining a sample region, structure defining a reagent circuit that includes metering chamber structure in series with said reagent circuit, first transfer valve structure for coupling said sample region to said reagent circuit on one side of said metering chamber structure, second transfer valve structure for coupling said reagent circuit to said reduced pressure reservoir structure on the side of said metering chamber structure remote from said first transfer valve structure,
- means connecting said reagent circuit of said sample insertion module to said reagent flow path of said gas diffusion unit,
- first position displacement pump structure for flowing reagent liquid through said reagent circuit, and said reagent flow path of said gas diffusion unit,
- second positive displacement pump structure for concurrently flowing buffer liquid through said buffer liquid flow path of said gas diffusion unit,
- means connecting said reagent circuit of said sample insertion module to said reagent flow path of said gas diffusion unit,
- means connecting said buffer liquid flow path of said gas diffusion unit to the inlet of said analysis structure,
- means for applying reduced pressure from said reservoir structure through said second transfer valve structure to reduce the pressure in said metering chamber structure for drawing reagent from said metering chamber structure through said second transfer valve structure and concurrently drawing sample from said sample region through aid first transfer valve structure into said metering chamber structure for replacing a quantity of reagent with a quantity of sample to be analyzed in a stream of reagent liquid in said reagent circuit to form an intact bubble-free composite stream, and
- flow control means for concurrently flowing a reagent stream including the inserted quantity of sample material from said reagent circuit through said gas diffusion unit and a stream of buffer liquid through said buffer liquid flow path and said analysis chamber,
- the inserted plug of sample material reacting with said reagent liquid to produce a gaseous constituent which diffuses across said membrane structure into said buffer liquid stream, and
- means coupled to said analysis chamber structure for responding to said gaseous constituent to provide data on a constituent of interest of said sample.

13. The system of claim 12 wherein said structure defining said reagent flow path includes structure defining a spiral groove, said structure defining said buffer liquid flow path includes structure defining a spiral groove, and said membrane structure is interposed between said spiral groove.

14. The system of claim 12 wherein said means connecting said reagent circuit of said sample insertion module to said reagent flow path of said gas diffusion unit includes a tubular member in coil form for promoting radial dispersion and bolus mixing.

15. The system of claim 12 wherein said module structure includes a face plate member that has a rigid surface,
- a flexible valve sheet member that has a surface that is softer and more resilient than said face plate member for mating engagement with said face plate surface,
- a network of channel portions in one of said members with a plurality of valve land portions, each said valve land portion being located between adjacent ones of said channel portions, the surfaces of said land portions being coincident with the surface of the member in which they are located,
- one of said channel portions defining said reduced pressure reservoir structure, a second one of said channel portions defining said reagent circuit, and a third of said channel portions defining said sample region, a portion of said reagent circuit channel and a portion of said sample channel extending through a valve region with a valve land between said adjacent channel portion so that to define said first transfer valve structure.

16. The system of claim 15 wherein each said transfer valve structure includes two parallel channels that extend through a valve region with a valve land extending through said valve region between said two parallel channels.

17. The system of claim 16 wherein said means coupled to said analysis chamber includes a pH electrode and a reference electrode 18. The system of claim 17 wherein said structure defining said reagent flow path includes structure defining a spiral groove, said structure defining said buffer liquid flow path includes structure defining a spiral groove, said membrane structure is interposed between said spiral grooves, and said means connecting said reagent circuit of said sample insertion module to said reagent flow path of said gas diffusion unit includes a tubular member in coil form for promoting radial dispersion and bolus mixing.

* * * * *

UNITED STATES PATENT AND TRADEMARK OFFICE
CERTIFICATE OF CORRECTION

PATENT NO. : 4,859,422

DATED : August 22, 1989

Page 1 of 2

INVENTOR(S) : Humayun Qureshi, et al.

It is certified that error appears in the above-identified patent and that said Letters Patent is hereby corrected as shown below:   On the title page:

In Section [56] References Cited, add the following patents:

--4,209,299    6/1980      Carlson            422/81
  4,299,794   11/1981      Kelley et al.      422/68

Col. 2, line 1, "AND+" should be --NAD+--.

Col. 2, line 9, "con" should be --conforming and mating--.

Col. 2, line 65, insert --of-- after "parameters".

Col. 2, line 66, insert --with-- after "seen".

Col. 3, line 45, "deionized" should be --de-ionized--.

Col. 4, line 7, "150 3" should be --150-3--.

Col. 4, line 9, "150 8" should be --150-8--.

Col. 4, line 10, "150 10 should be --150-10--.

Col. 4, line 47, "de energization "should be --de-energization.

Col. 4, line 62, insert --one-- after "about".

Col. 5, line 64, "150 4" should be --150-4--.

Col. 6, line 4, "150 9" should be --150-9--.

UNITED STATES PATENT AND TRADEMARK OFFICE
CERTIFICATE OF CORRECTION

PATENT NO. : 4,859,422
DATED : August 22, 1989
INVENTOR(S) : Humayun Qureshi, et al.

It is certified that error appears in the above-identified patent and that said Letters Patent is hereby corrected as shown below:

Col. 6, line 9, "150" should be --150-4--.

Col. 6, line 28, after "36" insert --to--.

Claim 1, col. 7, line 9, "regent" should be --reagent--.

Claim 2, col. 7, line 48, delete "said" after "said".

Claim 10, col. 9, line 28, delete "18" after "ple".

Claim 12, col. 9, line 60, "position" should be --positive--.

Claim 12, col. 10, line 10, "aid" should be --said--.

Signed and Sealed this

Sixth Day of November, 1990

Attest:

HARRY F. MANBECK, JR.

Attesting Officer     Commissioner of Patents and Trademarks